US009498595B2

(12) United States Patent
Spiel et al.

(10) Patent No.: US 9,498,595 B2
(45) Date of Patent: Nov. 22, 2016

(54) METHODS FOR PLACING A SYMPATHETIC BLOCK, CATHETERS, CATHETER ASSEMBLIES AND RELATED METHODS

(71) Applicant: CUSTOM MEDICAL APPLICATIONS, INC., Johnstown, NY (US)

(72) Inventors: Douglas J. Spiel, Farmers Branch, TX (US); N. Sandor Racz, Farmers Branch, TX (US)

(73) Assignee: Custom Medical Applications, Inc., Johnstown, NY (US)

(*) Notice: Subject to any disclaimer, the term of this patent is extended or adjusted under 35 U.S.C. 154(b) by 0 days.

(21) Appl. No.: 14/482,855

(22) Filed: Sep. 10, 2014

(65) Prior Publication Data
US 2015/0080854 A1    Mar. 19, 2015

Related U.S. Application Data

(60) Provisional application No. 61/878,956, filed on Sep. 17, 2013.

(51) Int. Cl.
*A61M 19/00* (2006.01)
*A61B 17/34* (2006.01)
*A61M 25/00* (2006.01)
*A61M 25/02* (2006.01)

(52) U.S. Cl.
CPC .......... *A61M 19/00* (2013.01); *A61B 17/3401* (2013.01); *A61B 17/3415* (2013.01); *A61M 2025/0059* (2013.01); *A61M 2025/0293* (2013.01)

(58) Field of Classification Search
CPC .................... A61M 19/00; A61M 2025/0286; A61M 2025/0007; A61B 17/3415
See application file for complete search history.

(56) References Cited

U.S. PATENT DOCUMENTS

| 3,902,501 | A  | 9/1975  | Citron et al.  |
|-----------|----|---------|----------------|
| 4,512,351 | A  | 4/1985  | Pohndorf et al. |
| 6,999,819 | B2 | 2/2006  | Swoyer et al.  |
| 7,330,764 | B2 | 2/2008  | Swoyer et al.  |
| 7,769,442 | B2 | 8/2010  | Shafer         |
| 7,912,555 | B2 | 3/2011  | Swoyer et al.  |
| 8,000,805 | B2 | 8/2011  | Swoyer et al.  |
| 8,036,756 | B2 | 10/2011 | Swoyer et al.  |
| 8,038,667 | B2 | 10/2011 | Racz et al.    |
| 8,206,343 | B2 | 6/2012  | Racz           |
| 8,287,496 | B2 | 10/2012 | Racz           |

(Continued)

FOREIGN PATENT DOCUMENTS

WO        03020365 A1    3/2003

*Primary Examiner* — Bradley Osinski
(74) *Attorney, Agent, or Firm* — TraskBritt, P.C.

(57) ABSTRACT

Methods of providing sympathetic nerve blocks comprise inserting a portion of a catheter into a subject. A distal end of the catheter is positioned on a lateral side of at least one vertebra of a vertebral column of the subject proximate to a portion of a sympathetic nervous system of the subject. A medication is supplied through the catheter to effect a sympathetic nerve block in the subject. Methods of alleviating pain in lower extremities of subjects comprise inserting a portion of a catheter into a subject and supplying a medication through the catheter. Catheters and catheter assemblies may be used in administering such sympathetic nerve blocks. Catheters and catheter assemblies may be used in administering medication to one or more of a peripheral nervous system of a subject and a spinal cord of a subject.

20 Claims, 9 Drawing Sheets

(56) References Cited

U.S. PATENT DOCUMENTS

| | | | | |
|---|---|---|---|---|
| 8,708,993 | B1* | 4/2014 | Shapiro | A61M 5/1454 604/131 |
| 2003/0045919 | A1* | 3/2003 | Swoyer | A61N 1/0558 607/122 |
| 2004/0097927 | A1* | 5/2004 | Yeung | A61B 17/1757 606/86 A |
| 2004/0210295 | A1* | 10/2004 | Brushey | A61M 25/001 607/120 |
| 2005/0060014 | A1 | 3/2005 | Swoyer et al. | |
| 2006/0129218 | A1 | 6/2006 | Swoyer et al. | |
| 2007/0050004 | A1 | 3/2007 | Swoyer et al. | |
| 2008/0125844 | A1 | 5/2008 | Swoyer et al. | |
| 2009/0018631 | A1 | 1/2009 | Snoderly | |
| 2011/0270269 | A1 | 11/2011 | Swoyer et al. | |

* cited by examiner

METHODS FOR PLACING A SYMPATHETIC BLOCK, CATHETERS, CATHETER ASSEMBLIES AND RELATED METHODS

CROSS-REFERENCE TO RELATED APPLICATION

This application claims the benefit of U.S. Provisional Patent Application Ser. No. 61/878,956, filed Sep. 17, 2013, the disclosure of which is hereby incorporated herein in its entirety by this reference.

TECHNICAL FIELD

The disclosure relates generally to medical procedures and medical device assemblies. In particular, the disclosure relates to catheters and catheter assemblies for use in administering medication to a subject and to methods utilizing catheters and catheter assemblies such as, for example, methods of placing a sympathetic block in a subject.

BACKGROUND

The advantages of continuous spinal anesthesia and continuous epidural anesthesia have been appreciated by anesthesiologists. Unlike conventional single-shot techniques, continuous spinal anesthesia (CSA) with an indwelling catheter placed into the subarachnoid space allows anesthesia of unlimited duration and the ability to carefully control the level of the block by administering repeated small, incremental doses of anesthetic. Similarly, while requiring relatively larger doses of anesthetic, continuous epidural anesthesia with an indwelling catheter placed in the epidural space may also be utilized to form a block in a subject. However, as pain management techniques are further developed, there has been a need to implement the benefits of these continuous-type anesthesia procedures into pain management procedures where long-term blocks may be used to minimize or alleviate pain in a subject. For example, where the continuous-type procedure is utilized to implement management of sensation in a subject (i.e., anesthesia), management of pain in a subject (i.e., analgesia), or both.

BRIEF SUMMARY

Described are methods of placing a sympathetic block in a subject (e.g., a mammal or bird) by placing a catheter proximate to a portion of the sympathetic nervous system of the subject. Also described are devices (e.g., catheters), kits, flexible needle assemblies, and catheter assemblies. In some embodiments, such catheters may be utilized, for example, to implement such a sympathetic block. Further described are catheters and catheter assemblies for use in administering medication to at least a portion of a nervous system of a subject, such as at least one of a peripheral nervous system of the subject and a spinal cord of the subject.

In some embodiments, methods of providing sympathetic nerve blocks to subjects in need thereof include inserting a portion of a catheter into a subject. A distal end of the catheter is positioned on a lateral side of at least one vertebra of a vertebral column of the subject proximate to a portion of a sympathetic nervous system of the subject. A medication is delivered through the catheter to create a sympathetic nerve block.

Also provided are methods of, for example, alleviating pain in lower extremities of a subject, the methods comprising inserting a portion of a catheter into a subject. A distal end of the catheter is positioned on a lateral side of at least one lumbar vertebra of the subject proximate to a portion of a sympathetic nervous system of the subject. An anesthetic and/or other agent is delivered through the catheter.

Further provided are catheter assemblies for use in administering medication to at least one of a peripheral nervous system of a subject and a spinal cord of a subject comprising a catheter. The catheter includes a flexible catheter tube having a proximal end and a distal end and at least one tine element coupled to an outer surface of the flexible catheter tube and positioned proximate the distal end of the catheter. The at least one tine element configured to enable insertion of the catheter through an introducer needle into a subject and to engage with at least a portion of the subject when the catheter is inserted within the subject.

Also provided are catheter assemblies for use in administering medication to at least one of a peripheral nervous system of a subject and a spinal cord of a subject comprising a catheter, a support structure, and a catheter connection hub. The catheter comprises a flexible catheter tube having a proximal end and a distal end. The support structure has a portion configured to be disposed within the flexible catheter tube of the catheter and is configured to support the catheter at least during insertion and placement. The proximal end of the flexible catheter tube is configured to contact a hub of the support structure when the portion of the support structure is received within the flexible catheter tube. The catheter connection hub is configured to receive and secure the proximal end of the catheter in the catheter connection hub.

Further provided are catheter assemblies for use in administering medication to at least one of a peripheral nervous system of a subject and a spinal cord of a subject, the catheter assemblies comprising a catheter, an introducer needle, a catheter connection hub, and a stylet. The catheter includes a flexible catheter tube having a proximal end and a distal end and at least one anchor element coupled to an outer surface of the flexible catheter tube and a reinforcing element positioned within the flexible catheter tube. The introducer needle is configured for inserting the catheter into the subject. The catheter connection hub is configured to receive and secure the proximal end of the catheter in the catheter connection hub. The stylet is configured for insertion through the catheter connection hub and into the catheter.

Also provided are catheter assemblies for use in administering a sympathetic nerve block to a subject, the catheter assemblies comprising a catheter, a support needle, a catheter connection hub, and a stylet. The catheter consists of a flexible catheter tube having a proximal end and a distal end. The support needle has a portion configured to be disposed within the flexible catheter tube and a first end having a tip configured to penetrate tissue of the subject during insertion of the support needle and the flexible catheter tube. The proximal end of the flexible catheter tube is configured to contact a needle hub of the support needle when the portion of the support needle is received within the flexible catheter tube. The catheter connection hub is configured to receive and secure the proximal end of the catheter in the catheter connection hub. The stylet is configured for insertion through the catheter connection hub and into the catheter.

DETAILED DESCRIPTION

The illustrations presented are not meant to be actual views of any particular catheter assembly, component of a catheter assembly, or act during a method of using a catheter assembly, but are merely idealized representations that are used to describe illustrative embodiments. Thus, the drawings are not necessarily to scale and relative dimensions may have been exaggerated for the sake of clarity. Additionally, elements common between figures may retain the same or similar numerical designation.

As used herein, the terms "distal" and "proximal" refer to an orientation of a catheter assembly with respect to a medical or veterinary practitioner when in use. For example, a distal end or portion of a catheter is the end or portion of the catheter closest to a subject and farthest from a practitioner during use of the catheter and a proximal end or portion of the catheter is the end or portion of the catheter closest to the practitioner and farthest from the subject during use of the catheter.

As used herein, the term "sympathetic block" refers to an at least partial blockade of the sympathetic nervous system of a subject, which may alter both the sympathetic component of pain (i.e., the pain itself) as well as any other physiologic manifestation of the sympathetic nervous system (e.g., vascular tone, sweating, and temperature). For example, a sympathetic block may be effected by injecting, e.g., local anesthetic in a region of sympathetic nerve tissue adjacent a lumbar vertebra of a subject, which may decrease vascular tone, thereby increasing blood flow, decreasing sweating, and increasing temperature. In certain areas, such as, for example, in the upper thoracic region, a sympathetic block may also decrease heart rate.

In some embodiments, the disclosure relates generally to methods of placing a sympathetic block in a subject and related medical device assemblies. More specifically, some embodiments of the disclosure relate to methods and related medical device assemblies that may enable a medical practitioner to administer a long-term sympathetic block to a subject.

In other embodiments, the disclosure relates generally to catheters and catheter assemblies that may be used in administering medication to one or more of a peripheral nervous system of a subject and a spinal cord of a subject.

Figure 1:
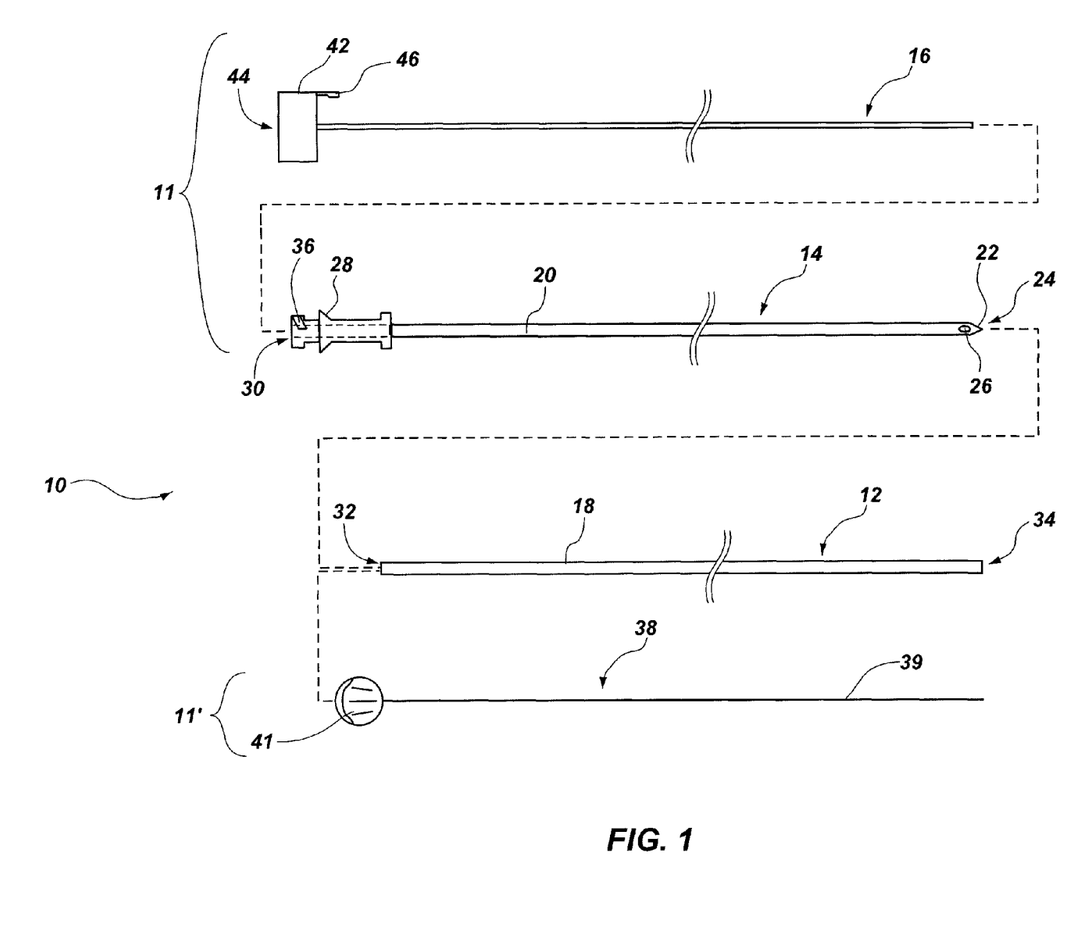
FIG. 1 is an exploded plan assembly view of a catheter assembly.

FIG. 1 is an exploded plan assembly view of a catheter assembly 10 that may be used for positioning a catheter to provide medication to a subject (e.g., to provide a sympathetic nerve block). As shown in FIG. 1, the catheter assembly 10 includes a catheter 12 and a support structure 11 that may be at least partially positioned within the catheter 12 during placement and positioning of the catheter 12 within a subject. In some embodiments, the support structure 11 includes an introducer needle or cannula (e.g., a support needle 14 for a catheter-over-needle configuration) configured for at least partial insertion (e.g., implanting) into the catheter 12 and a solid stylet 16 that may be at least partially positioned within the support needle 14. In other embodiments, the support structure 11 includes only the support needle 14 or only the solid stylet 16. In still other embodiments, a support structure 11' includes a stylet wire assembly 38 that may be at least partially positioned within at least one of the catheter 12 and the support needle 14. In some embodiments, the catheter assembly 10 is somewhat similar to, for example, the flexible needle assemblies described in U.S. Pat. No. 8,287,496 to Racz, issued Oct. 16, 2012, the disclosure of which is incorporated herein in its entirety by this reference. The support structure 11 (e.g., one or more of the support needle 14 and the solid stylet 16) may be disposable in some embodiments and reusable in other embodiments.

The catheter 12 may comprise a flexible catheter tube 18 configured for insertion into a subject to provide a conduit through which other devices or substances (e.g., a stylet, a probe, a fluid, a medication, neuromuscular blocking agent, etc.) may be conveyed. In some embodiments, the catheter 12 has an outer diameter of between approximately 21 gauge and 24 gauge, although the catheter 12 may have different diameters depending on the particular procedures to be used and the particular devices or substances to be placed within or conveyed through the catheter 12. Conventional materials (e.g., medical grade plastics) and methods of forming may be used in construction of the catheter 12. The catheter 12 may be reinforced with a flat ribbon internal spring, an internal or external wire wrap, or other integral reinforcing structure to resist collapse, kinking, or breakage of the catheter 12 as discussed below. Alternative materials, and various materials in combination, also may be used to construct the catheter 12. In some embodiments, at least a portion of an exterior surface of the catheter 12 comprises a slippery, nonstick surface to ease insertion and removal of the catheter 12. For example, the exterior surface of the catheter 12 may be coated or partially coated with polytetrafluoroethylene (e.g., TEFLON®). In some embodiments, at least a portion of an exterior surface of the catheter 12 comprises an antibacterial coating. Suitable materials and configurations produce a catheter 12 that is sufficiently stiff and has a sufficiently high tensile strength to maintain structural integrity during insertion, while in the body, and during retraction from a subject. The catheter 12 desirably possesses sufficient transverse flexibility to deform and accommodate subject motion to reduce irritation from the presence of a foreign body.

The optional support needle 14 may comprise a cannula 20 defining a tip 22 configured to penetrate tissue during insertion of the catheter assembly 10 at a distal end 24 of the support needle 14. The tip 22 comprises, for example, a non-cutting piercing point (e.g., a pencil-point tip) in some embodiments. In other embodiments, the tip 22 is rounded or otherwise comprises a blunt shape. In still other embodiments, the tip 22 comprises a cutting point. The cannula 20 may comprise at least one opening 26 at or near the tip 22 to provide a passageway from an internal bore of the cannula 20 to an exterior of the cannula 20. For example, the cannula 20 may include a plurality of openings 26 through a sidewall of the cannula 20 or may include a single axial opening at the tip 22. In some embodiments, the cannula 20 has an outer diameter of between approximately 21 gauge and 24 gauge, although the cannula 20 may have different diameters depending on the particular procedures to be used and the particular devices or substances to be conveyed through the cannula 20 or through which the cannula 20 is to be conveyed.

The optional support needle 14 may comprise a needle hub 28 at a proximal end 30 of the support needle 14. The needle hub 28 may be transparent, translucent, or may include a transparent or translucent window to enable a practitioner to view other devices or substances as they are conveyed through the needle hub 28. The needle hub 28 may be formed around or otherwise coupled to the cannula 20 such that the internal bore of the cannula 20 extends from the proximal end 30 of the support needle 14 to or near the distal end 24 of the support needle 14 to provide a continuous passageway through which other devices or substances (e.g., a stylet, a fluid, or a medication) pass in some embodiments. The needle hub 28 may include a connector 36 (e.g., a LUER-LOK® connector), or other attachment structure, for easy and secure connection with infusion tubing, injection ports, syringes, pumps, or other medical fluid transfer apparatus. The support needle 14 may be reinforced with a flat ribbon internal spring, an internal or external wire wrap, or other reinforcing structure.

In embodiments where the support structure 11 of the catheter assembly 10 comprises a support needle 14, the support needle 14 is at least partially inserted into the catheter 12. For example, the tip 22 of the support needle 14 may be inserted into a proximal end 32 of the catheter 12, through the catheter 12, and extended beyond a distal end 34 of the catheter 12. For example, the tip 22 of the support needle 14 may extend between about 0.5 mm and about 5.0 mm beyond the distal end 34 of the catheter 12 when the support needle 14 is assembled with the catheter 12. The proximal end 32 of the catheter 12 is secured to the needle hub 28 (e.g., using a friction fit) to maintain relative positioning of the catheter 12 and the support needle 14 during insertion and placement in some embodiments. In other embodiments, relative positioning is maintained using mechanical interference simply by contacting the proximal end 32 of the catheter 12 to the needle hub 28.

In certain embodiments, the catheter 12 is configured to be inserted into the subject within the cannula 20 of the support needle 14 or within the cannula of another needle such as, for example, an introducer needle (e.g., a flexible introducer cannula (FIC) as discussed below with reference to FIGS. 3 and 4). In other words, the catheter 12 is configured for insertion into the subject via the cannula of needle rather than the catheter-over-needle configuration discussed above.

The optional solid stylet 16 may be configured for at least partial insertion into the catheter 12 or into the support needle 14 during insertion of the catheter assembly 10 into a subject. The solid stylet 16 may act to prevent the entry of extraneous tissue, body fluids, or other material into the distal end 34 of the catheter 12 or into the support needle opening 26 during insertion. The solid stylet 16 may also serve as a "stiffening" portion of the catheter assembly 10 providing extra support and stiffness to the entire assembly 10. The solid stylet 16 may include a stylet hub 42 at a proximal end 44 of the solid stylet 16. The stylet hub 42 may be configured to attach to the connector 36 of the needle hub 28 to secure the solid stylet 16 in place using a tab 46 in embodiments where the support structure 11 comprises both the support needle 14 and the solid stylet 16. In other embodiments, where the solid stylet 16 is used within the catheter 12 without the support needle 42, the hub of the solid stylet 16 includes any suitable structure that interfaces with the catheter 12 (e.g., a structure that abuts the proximal end 32 of the catheter 12 in order to retain the catheter 12 on the solid stylet 16).

In embodiments where the support structure 11 comprises both the support needle 14 and the solid stylet 16, the solid stylet 16 is at least partially inserted into the support needle 14, which may be at least partially inserted into the catheter 12. When fully inserted into the support needle 14, the solid stylet 16 may obstruct the openings 26 and the stylet hub 42 may be attached to the needle hub 28. In embodiments where the support structure 11 comprises the solid stylet 16, and not the support needle 14, the solid stylet 16 may be at least partially inserted directly into the catheter 12. When fully inserted into the catheter 12, the solid stylet 16 may obstruct the distal end 34 of the catheter 12 to prevent materials (e.g., body tissues or fluids) from entering the catheter 12.

The optional stylet wire assembly 38 may include a stylet wire 39, which may be coupled to a stylet cap 41. The stylet wire 39 may comprise a single wire, a single tube, a plurality of intertwined or interwoven wires, or a plurality of intertwined or interwoven tubes (see, e.g., the above-incorporated U.S. Pat. No. 8,206,343). The stylet wire 39 may be configured to reinforce (e.g., by increasing stiffness, by reducing the likelihood of restriction of flow if such components are bent (i.e., kinked) during or after insertion into a subject, or both) components of the catheter assembly 10 (e.g., the catheter 12). For example, the stylet wire assembly 38 is configured to reinforce the catheter 12 after the catheter 12 has been positioned within a subject and the support structure 11 has been removed in some embodiments. In other embodiments, the support structure 11' comprises the stylet wire assembly 38, not the support needle 14 or the solid stylet 16, and the stylet wire assembly 38 may reinforce the catheter 12 during and after positioning within the subject. The stylet wire assembly 38 may comprise materials, such as, for example, medical grade stainless steel or medical grade titanium. In some embodiments, the stylet cap 41 is configured to attach to another connector to secure the stylet wire assembly 38 in place using, for example, the stylet cap connections described in International Application No. PCT/US2011/001828 to Racz et al., filed Oct. 28, 2011, published as WO 2013/062504 A1 on May 2, 2013, the disclosure of which is incorporated herein in its entirety by this reference, a threaded connection, or a LUER-LOK® joint. In other embodiments, the stylet wire assembly 38 comprises a stylet wire 39 and lack any stylet cap.

In still other embodiments, the stylet wire assembly 38' comprises a stylet wire 39 coupled to a removable catheter connection hub 66, as discussed in further detail in connection with FIG. 8. In such embodiments, the proximal end 32 of the catheter 12 is secured within a catheter-receiving portion 74 of the removable catheter connection hub 66.

In embodiments where the support structure 11' comprises the stylet wire assembly 38, the stylet wire assembly 38 is at least partially inserted directly into the catheter 12. In other embodiments where the support structure 11' comprises the stylet wire assembly 38, the stylet wire assembly 38 is at least partially inserted into the support needle 14, which may be at least partially inserted into the catheter 12.

In some embodiments, the stylet wire assembly 38 is configured such that the distal end of the stylet wire 39 extends past the distal end of the catheter in which it is positioned (e.g., in an open ended catheter). In such an embodiment, the distal end of the stylet wire 39 acts as an atraumatic blunt protrusion.

Figure 2:
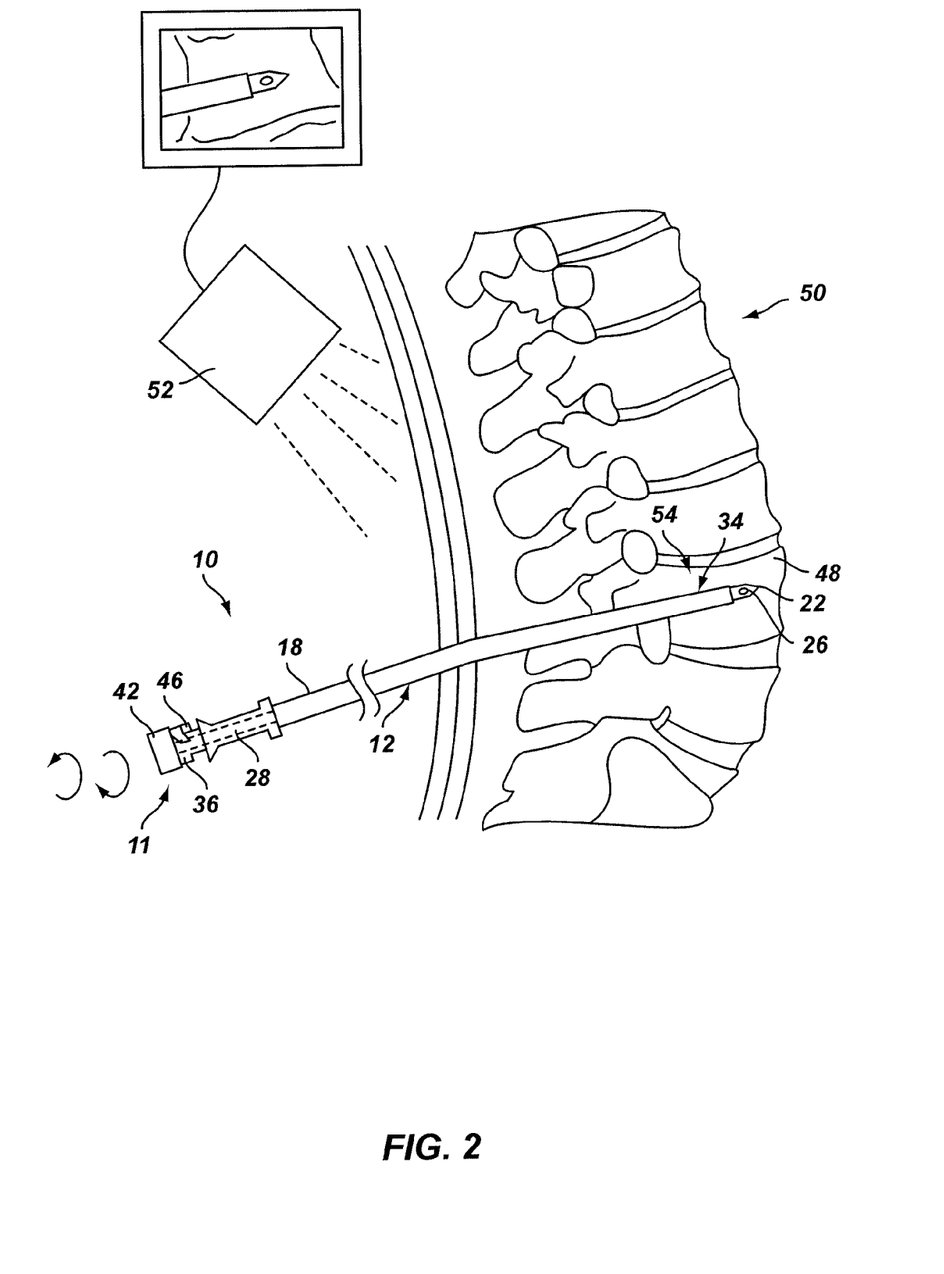
FIG. 2 shows a catheter assembly during placement at a subject's lumbar region.

Referring to FIG. 2, a portion of the catheter assembly 10 may be inserted into a subject and placed to, for example, effect a sympathetic block after the catheter assembly 10 has been assembled. In some embodiments, the catheter assembly 10 is inserted through introducer needle (e.g., a flexible introducer cannula (FIC) such as a peel-away FIC) such as, for example, those described in U.S. Pat. No. 4,512,351, issued Apr. 23, 1985 to Pohndorf, the disclosure of which is incorporated herein in its entirety by this reference. Briefly, a suitable FIC may comprise an introducer needle (e.g., a Tuohy needle) inserted through a sheath (e.g., a peel-away sheath), and may be disposable after use. A stylet (not shown) may be located within the FIC during insertion and removed from within the FIC after insertion is complete. After insertion and positioning the FIC, the sheath may be peeled apart and secured in place and the introducer needle may be withdrawn to accommodate insertion of the catheter assembly 10. In other embodiments, the catheter assembly 10 is inserted through the introducer needle, and the introducer needle may be withdrawn over the one or more components of the catheter assembly 10 (e.g., the catheter 12). In yet other embodiments, the catheter assembly 10 is inserted directly into a subject on its own, without using a FIC or other introducer cannula.

The catheter assembly 10 may be advanced into the subject (e.g., through a FIC) until the distal end 34 of the catheter 12 of the catheter assembly 10 is positioned on a lateral side of at least one vertebra 48 of a vertebral column 50 of the subject proximate to a portion of a sympathetic nervous system of the subject. For example, the distal end 34 of the catheter 12 may be positioned on a lateral side of a lumbar vertebra 48 of the subject proximate to a region of sympathetic nerve tissue. As a specific, nonlimiting example, the distal end 34 of the catheter 12 may be positioned on a lateral side of the L4 vertebra 48 of the subject proximate to a region of sympathetic nerve tissue. The distal end 34 of the catheter 12 may be positioned, for example, posterior to an anterior vertebral bodyline of a vertebra 48 proximate to a region of sympathetic nervous tissue.

Advancement and positioning of the catheter assembly 10 may be monitored using imaging equipment 52. For example, radiography (e.g., fluoroscopy) may produce real-time images of the internal structure of the body and the catheter assembly 10 as it is inserted and positioned within the body to enable a practitioner to accurately position the distal end 34 of the catheter 12 on the lateral side of the vertebra 48 proximate to the portion of the sympathetic nervous system of the subject. In other embodiments, ultrasound or other real-time medical imaging techniques are used to monitor and verify advancement and positioning of the catheter assembly 10.

In some embodiments, a distal portion 54 of the catheter assembly 10 (e.g., a distal portion of the catheter 12 and the underlying support structure 11) is optionally bent or curved. Such a bent or curved distal portion 54 may enable a practitioner to steer the catheter assembly 10 by twisting the catheter assembly 10, as indicated in FIG. 2 by rotating arrows, to reorient the direction in which the bent or curved distal portion 54 points. In addition, such a bent or curved distal portion 54 may enable the catheter assembly 10 to conform more closely to a curved profile of the lateral side of the vertebra 48 at which the distal end 34 of the catheter 12 is positioned, which may enable more accurate and precise placement of the distal end 34 of the catheter 12. The distal portion 54 of the catheter assembly 10 may be bent or curved by the practitioner after assembly and prior to insertion. For example, the practitioner may permanently deform (i.e., plastically deform) the support structure 11 or 11' within the catheter 12 to impart a bend or curve to the distal portion 54 of the catheter assembly 10. In other embodiments, the support structure 11 or 11' is pre-bent or pre-curved, by the practitioner, by the manufacturer, or by some other handler of the support structure 11 or 11' before assembly to impart a bend or curve to the distal portion 54 of the catheter assembly 10.

After the distal end 34 of the catheter 12 has been positioned on the lateral side of the vertebra 48 proximate to the portion of the sympathetic nervous system, the support structure 11 or 11' is withdrawn from the catheter 12 in some embodiments. In addition, the peel-away sheath may optionally be withdrawn over the catheter 12 in embodiments where a flexible introducer cannula (FIC) was used to introduce the catheter assembly 10 into the subject. In some embodiments, the support structure 11 or 11' is withdrawn simultaneously as a single unit. In embodiments where the support structure 11 comprises both the support needle 14 and the solid stylet 16, the solid stylet 16 is withdrawn from within the support needle 14, and the support needle 14 may subsequently be withdrawn from within the catheter 12. In such embodiments, withdrawal of the solid stylet 16 from within the support needle 14 may unseal the opening 26 in the cannula 20 of the support needle 14. In other embodiments, the support structure 11 or 11' may remain within the catheter 12 after positioning. For example, the support structure 11' may remain within the catheter 12 in embodiments where the support structure 11' comprises a stylet wire assembly 38' including a removable catheter connection hub 66 (see FIG. 8).

In some embodiments, a medication (e.g., an anesthetic, an analgesic, neuromuscular blocking agent, sedative, or other biologically active agent) is supplied through the support needle 14 and out of the opening 26 to initiate a sympathetic block. For example, the practitioner may supply a quantity of the medication by positioning a hypodermic needle or other medication transfer device within the connector 36 of the needle hub 28 and forcing flow of the medication through the support needle 14 within the catheter 12 and out the opening 26 on the lateral side of the vertebra 48 at which the distal end 24 of the support needle 14 is positioned in embodiments where the support structure 11 comprises a support needle 14. In other embodiments, such a medication is supplied through the introducer needle prior to inserting the catheter assembly 10 and placing the catheter 12. In still other embodiments, no medication may be supplied through the support needle 14 or the introducer needle.

In some embodiments, the introducer needle utilized to position the catheter 12 within the subject and/or support structure 11 or 11' of the catheter 12 may be configured to have a stimulating portion used to "stim" or stimulate the nerves of the subject.

Figure 3:
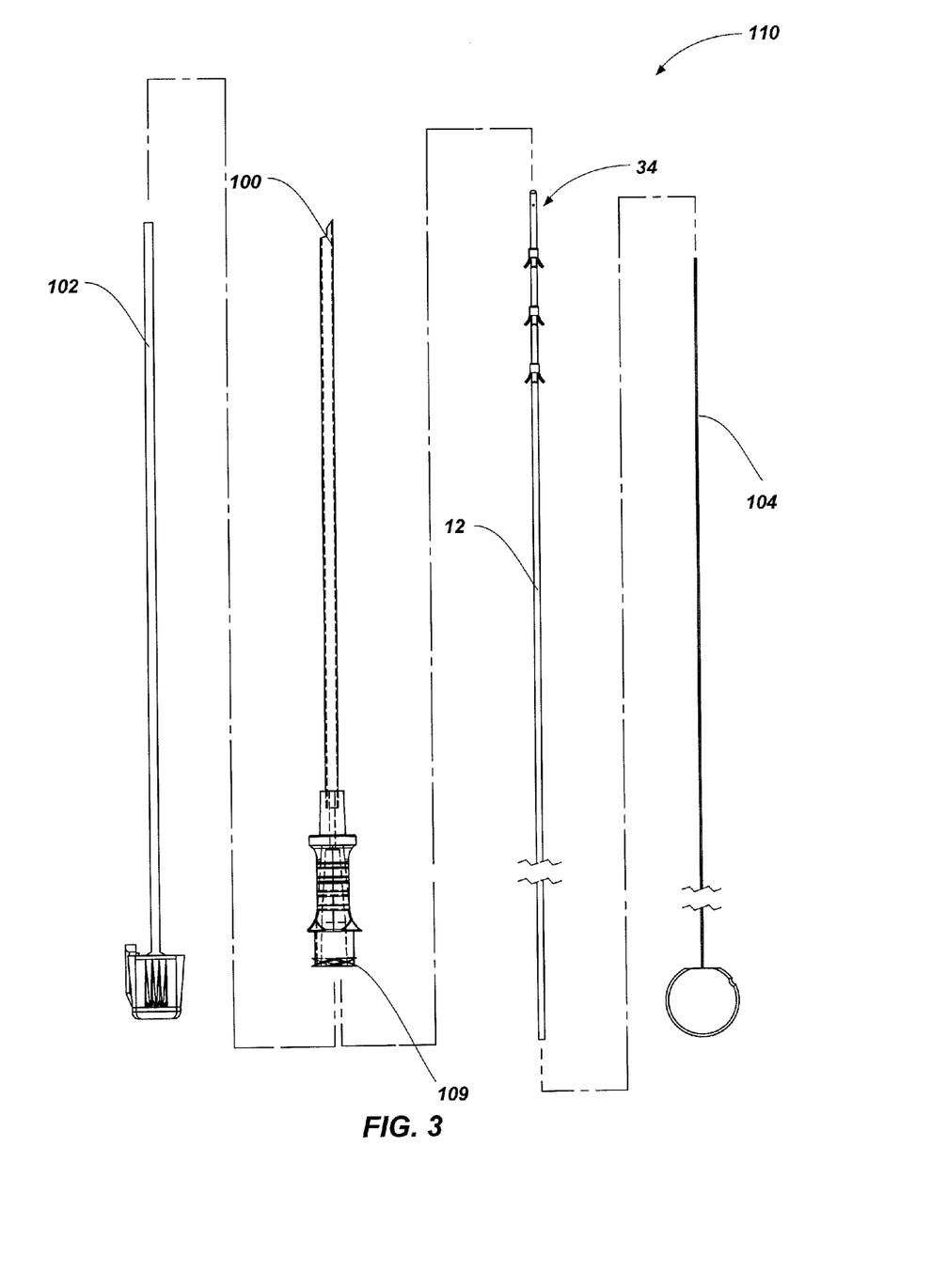
FIG. 3 is an exploded plan assembly view of a catheter assembly.

FIG. 3 is an exploded plan assembly view of a catheter assembly 110. The catheter assembly 110 may be similar to and may be utilized in the same or similar methods as the catheter assembly 10 discussed above with reference to FIGS. 1 and 2. As shown in FIG. 3, the catheter assembly 110 includes an introducer needle (e.g., a flexible introducer cannula (FIC) 100), stylet 102, which may be similar to stylet 16 discussed above with reference to FIG. 1, the catheter 12, and a stylet wire assembly 104, which may be similar to stylet wire assembly 38, 38' discussed above and below with reference to FIGS. 1 and 8.

The catheter 12 is inserted into the subject with the flexible introducer cannula (FIC) 100, which includes a sheath and introducer needle where a tip 105 of the introducer needle protrudes from the sheath. In some embodiments, support structure (e.g., stylet 106) is located within the FIC 100 during insertion and removed from within the FIC 100 after insertion is complete. In some embodiments, the catheter 12 is reinforced for insertion through the FIC 100. For example, the stylet wire assembly 104 is placed within the catheter 12 during insertion and may be removed from within the catheter 12 after insertion is complete or left within the catheter 12 to, for example, prevent kinking of the catheter 12 as it resides in the subject as discussed below.

As above, in some embodiments, the FIC 100 includes a needle hub 108 with a connecting portion 109 for connecting with infusion tubing, injection ports, syringes, pumps, or other medical fluid transfer apparatus.

Figure 4:
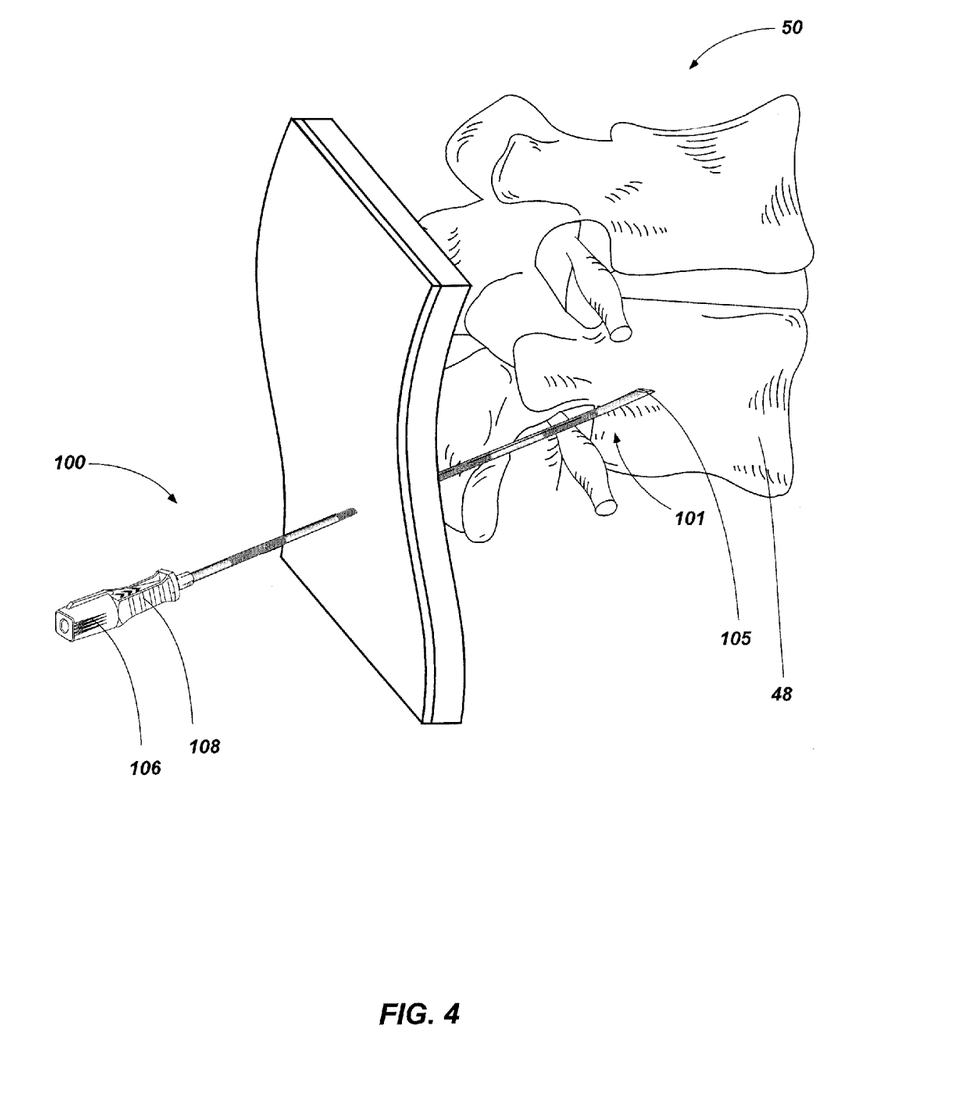
FIG. 4 shows the catheter assembly shown in FIG. 3 during placement at a subject's lumbar region.

FIG. 4 shows the catheter assembly shown 110 in FIG. 3 during placement at a subject's lumbar region. As shown in FIGS. 3 and 4, a distal end 101 of the FIC 100 may be positioned proximate the vertebral column 50 of the subject. The catheter 12 may be advanced into the subject (after removing the stylet 106, if implemented) through the FIC 100 (e.g., using imaging equipment 52 (FIG. 2)) until the distal end 34 of the catheter 12 of the catheter assembly 110 is positioned on a lateral side of at least one vertebra 48 of the vertebral column 50 of the subject proximate to a portion of the sympathetic nervous system of the subject. For example, the distal end 34 of the catheter 12 may be positioned on a lateral side of the lumbar vertebra 48 (e.g., the L4 vertebra) of the subject proximate to a region of sympathetic nerve tissue.

Figure 9:
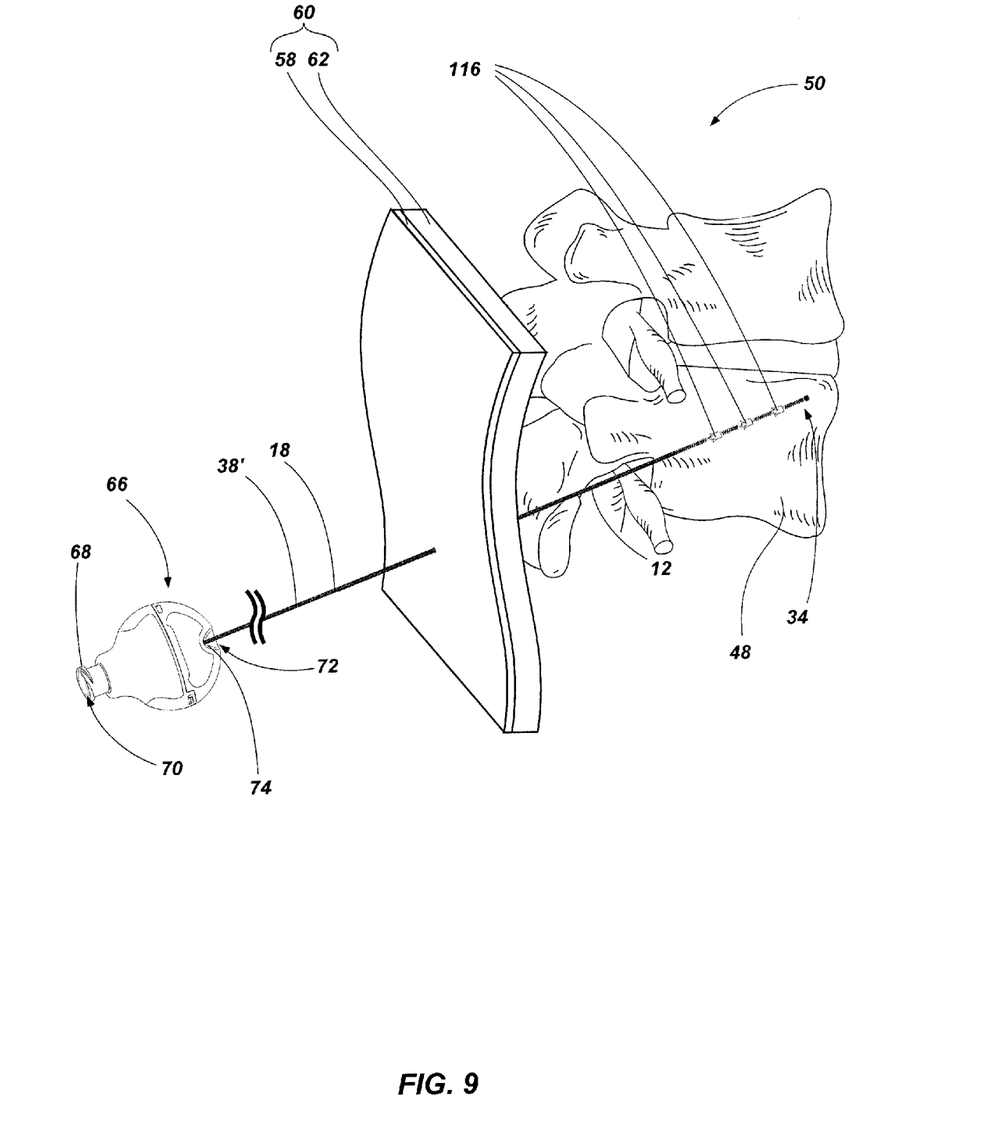
FIG. 9 is a side view of a catheter assembly configured for attachment to a pump.

After the catheter 12 is positioned in the subject, at least of a portion of the FIC 100 (e.g., the introducer needle and/or sheath) may be removed leaving the catheter 12 placed within the subject (see, e.g., FIG. 9). In some embodiments, a stylet wire assembly (e.g., stylet wire assembly 104) is inserted into the catheter 12 while the at least of a portion of the FIC 100 is removed. The stylet wire assembly 104 may then be removed from or retained in the catheter 12.

In some embodiments, the practitioner may tunnel the catheter 12 such that the catheter 12 exits the subject at a location remote from the initial incision site of the needle (e.g., the support needle 14 (FIGS. 1 and 2) and/or the introducer needle (e.g., FIC 100)). For example, the practitioner may tunnel the catheter 12 four to six inches (10.16 to 15.24 centimeters) to the side of the initial incision site of the needle. As known in the art, tunneling the catheter 12 to exit the subject at a location remove from the incision site of the needle may act to provide stability to the catheter 12 and may reduce the risks of infection.

After the catheter 12 has been placed, a cuff (not shown) may be secured around the catheter 12 and sutured to the incision to secure the catheter 12, or the catheter 12 may be secured using an adhesive (e.g., an adhesive bandage) over the incision. In other embodiments, a portion of the catheter 12 may be secured to the subject without tunneling the catheter 12 (e.g., a non-tunneled catheter), for example, by securing a cuff (not shown) around the catheter 12 and suturing the cuff to the subject or by an adhesive (e.g., an adhesive bandage).

Figure 5:
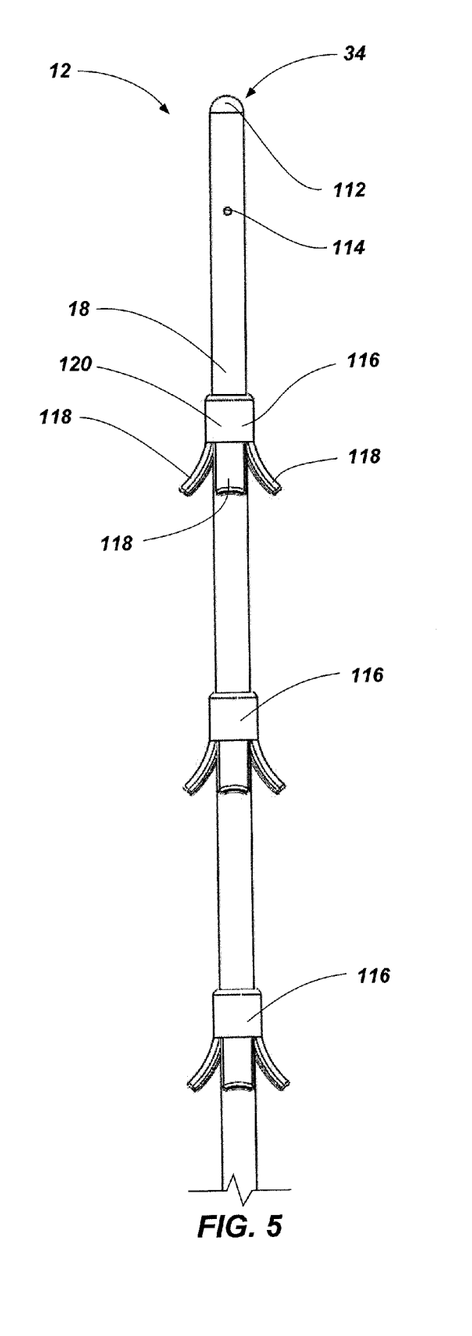
FIG. 5 shows a catheter in accordance with embodiments of the present disclosure.

FIG. 5 shows an embodiment of the catheter 12 that may be utilized in placing providing a sympathetic nerve block. Referring to FIG. 5, a distal portion of the catheter 12 may include a closed end 112 and one or more apertures or openings 114 may be formed in a sidewall of the flexible catheter tube 18 so as to enable the fluid transported by the catheter 12 to pass therethrough. In some embodiments, the catheter 12 includes openings 114 (e.g., two openings 114) positioned proximate the distal end 34 of the catheter 12 (e.g., within about 10 millimeters, for example, about 2.5 millimeters from the distal end 34) circumferentially spaced about the catheter 12 (e.g., 180° apart). In other embodiments, the catheter 12 includes openings 114 that are spaced along the length of the catheter 12. It is noted that while the embodiment of FIG. 5 shows the catheter tube 18 as having the closed end 112, in other embodiments, the catheter includes one or more openings at the distal end 34 thereof.

The catheter 12 includes one or more elements for anchoring the catheter 12 within a subject (e.g., to at least partially prevent movement of the catheter 12 within the subject. For example, the catheter 12 may include one or more tine elements 116 (e.g., one, two, three, or more tine elements 116) coupled to the catheter tube 18 (e.g., an outer portion of the catheter tube 18) and spaced (e.g., equally spaced) along the distal portion of the catheter 12. Each tine element 116 may include one or more tines 118 (e.g., one, two, three, or more tines) spaced (e.g., equally spaced) about the circumference of the catheter tube 18. Each of the tines 118 may extend from a base portion 120 of the tine element 116 that is secured to the catheter tube 18 (e.g., via interference fit, adhesion, or other suitable attachment methods). In some embodiments, the tine elements 116 are positioned at equally-spaced increments along the catheter 12 (e.g., 10 millimeters from the distal end 34 of the catheter and 10 millimeters apart from each adjacent tine element 116).

Each of the tines 118 of the tine elements 116 may be flexible such that the tines 118 may be positioned (e.g., forced) proximate (e.g., adjacent) the catheter tube 18 during the placement of the catheter 12 into the subject (e.g., while the catheter 12 is fed through an introducer needle as discussed above). For example, the tine element 116 may be formed such that the portion the tines 118 that are positioned further away from the hub portion 120 extend outwardly (e.g., radially) from the catheter tube 18.

The tine elements 116 may be utilized to at least partially secure the catheter 12 within the subject. For example, the tine elements 116 may at least partially retain the catheter 12 within the subject as shown in FIG. 9 and to at least prevent the catheter 12 from moving within the subject. The tine elements 116 may anchor the catheter 12 by engaging with one or more portions of the subject. For example, the tine elements 116 may engage with a portion of the subject's muscular system (e.g., the psoas major muscle) or other tissue to at least partially retain the catheter 12 in a desired position within the subject.

Figure 6:
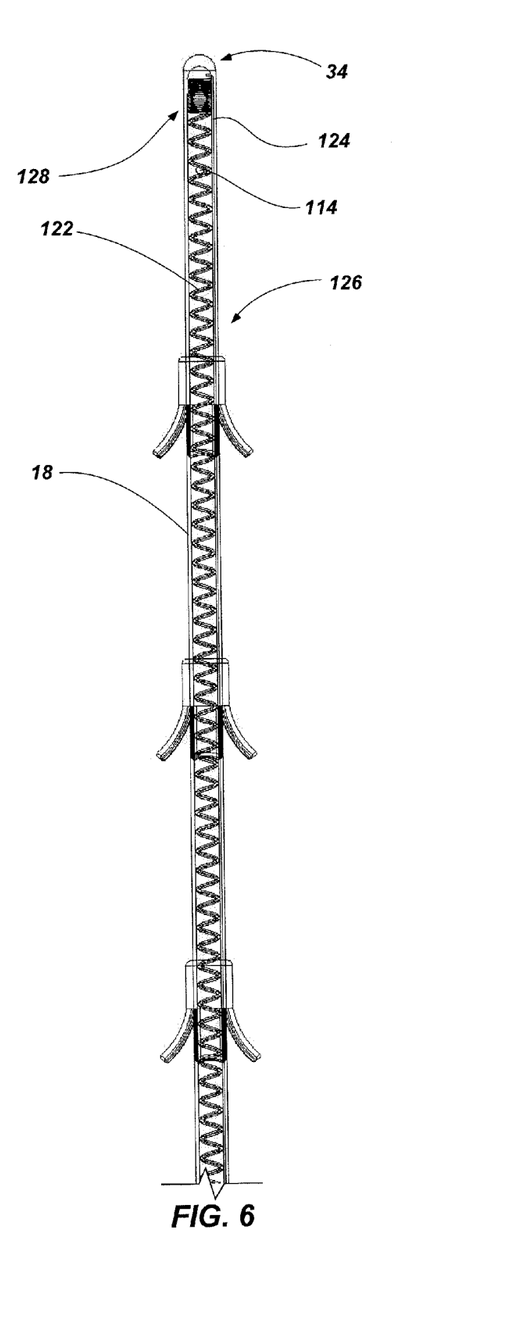
FIG. 6 is a cross-sectional view of a catheter (e.g., the catheter shown in FIG. 4) in accordance with embodiments of the present disclosure.

FIG. 6 is a cross-sectional view of an embodiment of a catheter (e.g., the catheter 12 shown in FIG. 5). As shown in FIG. 6, the catheter 12 may include one or more reinforcement elements (e.g., an internal helical coil spring 122, a filament or wire 124, or combinations thereof). For example, the catheter 12 may comprise a reinforced catheter having an elongated tubular outer wall reinforced by an internal helical coil spring and an internal filament such as, for example, that disclosed in U.S. Pat. No. 8,206,343 to Racz, issued Jun. 26, 2012, the disclosure of which is incorporated herein in its entirety by this reference.

As depicted, the catheter 12 includes the internal helical coil spring 122 and the wire 124. Each of the helical coil spring 122 and the wire 124 may be formed from medical grade metallic or synthetic material (e.g., stainless steel). The coil spring 122 may include an open portion 126 exhibiting a pitch (i.e., the distance from the center of one coil to the center of an adjacent coil) that enables fluid to flow between coils of the coil spring 122 and exit the catheter tube 18 through the openings 114. The coil spring 122 may include a closed portion 128 exhibiting a pitch less than the pitch of the open portion 126. For example, the coils of the coil spring 122 at the closed portion 128 are positioned relatively more close together (e.g., abutting each other) as compared to the open portion 126 proximate the distal end 34 of the catheter 12.

Figure 7:
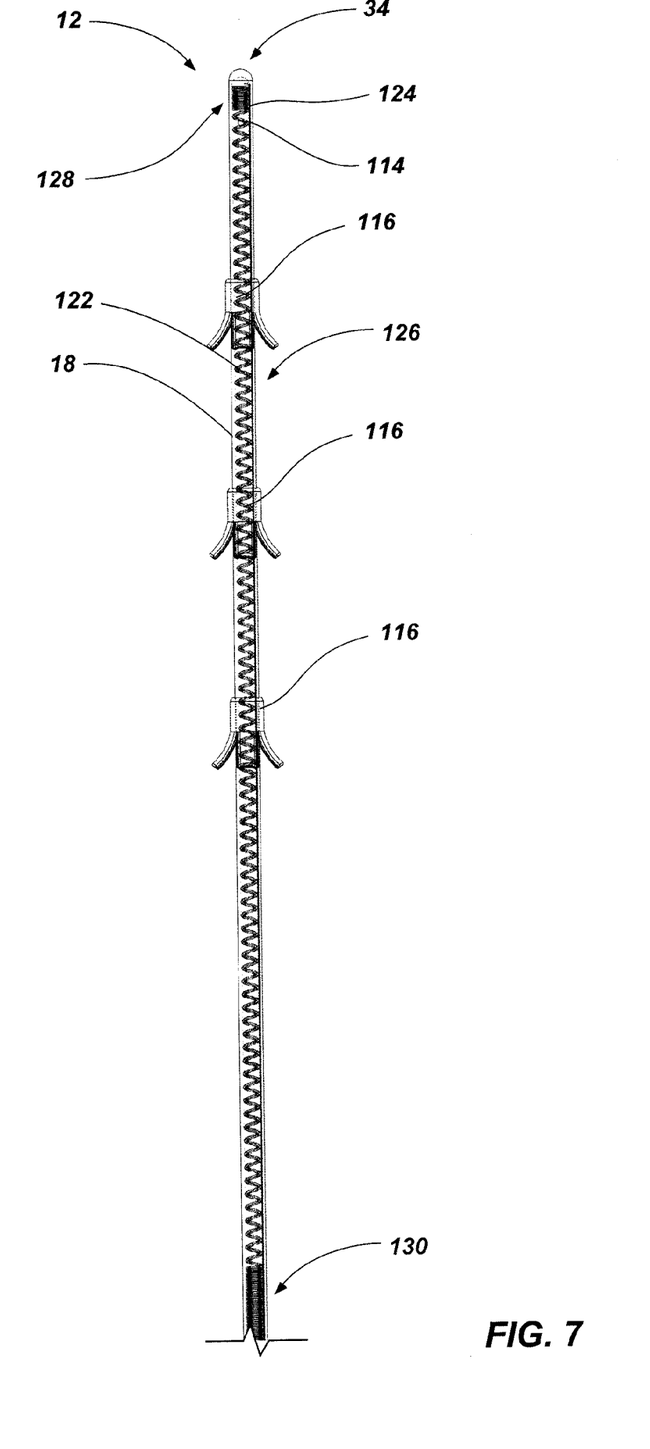
FIG. 7 is another cross-sectional view of the catheter shown in FIG. 6.

FIG. 7 is another cross-sectional view of the catheter 12 shown in FIG. 6. As shown in FIG. 7, the coil spring 122 may include a closed portion 130 exhibiting a pitch less than the pitch of the open portion 126 at a portion of the coil spring 122 extending toward the proximal end 32 (FIG. 1) of the catheter 12. For example, the coils of the coil spring 122 at the closed portion 130 are positioned relatively more close together (e.g., abutting each other) as compared to the open portion 126 proximate the distal end 34 of the catheter 12. As depicted, the coil spring 122 may include the open portion 126 proximate the openings 114 (e.g., at the distal portion of the catheter) and at least a majority of the remainder of the coil spring 122 (e.g., the portion positioned distal to the openings 114) may be formed as the closed portion 130.

Referring back to FIG. 6, the wire 124 may be positioned proximate the catheter tube 18 (e.g., abutting the catheter tube 18, embedded within the catheter tube 18). For example, the wire 124 may be positioned (e.g., secured or bound) between the coil spring 122 and the catheter tube 18 and may extend along the length of the coil spring 122 and/or the length of the catheter 12. In some embodiments, the wire 124 is formed as a ribbon (e.g., a flat ribbon having a lateral width that is greater than a thickness of the ribbon or, in other words, a rectangular lateral cross section). The wire 124 may be attached to the coil spring 122 proximate the distal end 34 of the catheter 12. For example, a distal end of the wire 124 may be bent and attached (e.g., welded) to the coil spring 122. In some embodiments, a metallic ball (e.g., a weld ball 132) is formed at the distal end 34 of the catheter 12 to join the wire 124 and coil spring 122. In some embodiments, a proximal end of the wire 124 is secured to the coil spring 122 at a distal portion of the catheter 12. For example, the proximal end of the wire 124 may be secured to the closed section 130 of the coil spring 122 proximate the open section 126 of the coil spring 122. In other embodiments, the proximal end of the wire 124 is secured to the coil spring 122 near the proximal end 34 (FIG. 1) of the catheter 12.

In some embodiments, the reinforcement elements (e.g., the internal helical coil spring 122 and/or the wire 124) act to stiffen the catheter 12 in one or more of the lateral and longitudinal (i.e., radial and axial) directions. For example, the coil spring 122 may laterally stiffen (e.g., reduce flexibility) the catheter 12. The closed portions 128, 130 of the coil spring 122 may be relatively stiffer than the open portion 126 of the coil spring 122. The wire 124 may act to longitudinally strengthen the catheter 12 and may act to at least partially prevent axial lengthening of the coil spring 122 (e.g., the open portion 126 of the coil spring 122).

Figure 8:
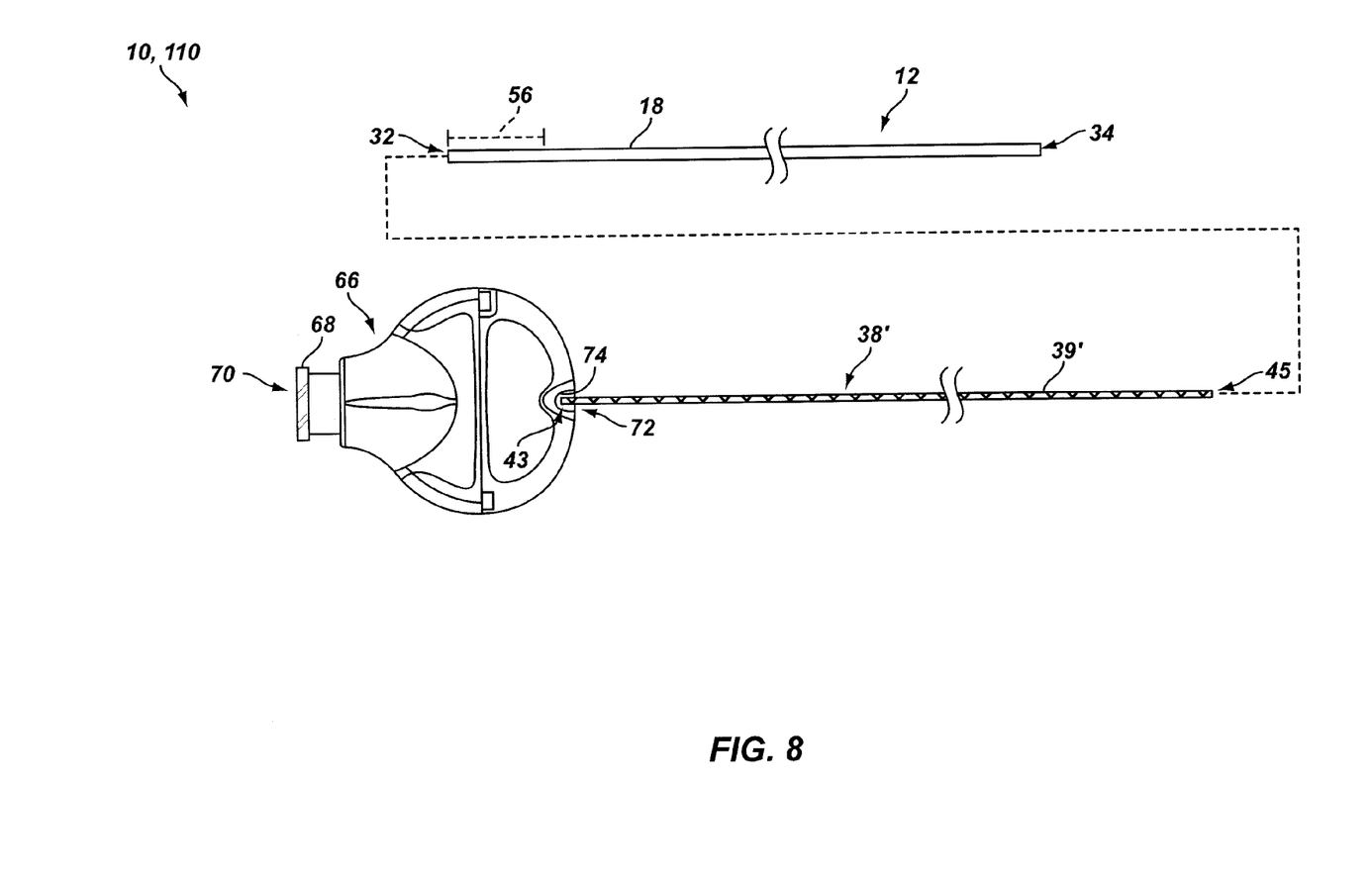
FIG. 8 is an exploded plan assembly view of a catheter assembly.

Referring to FIG. 8, the catheter 12 may be assembled with other components of the catheter assembly 10, 110 that are configured for attachment to a supply of medication (e.g., a pump). For example, the catheter 12 (e.g., which may be formed with one or more tine elements 116 and/or reinforcing elements as discussed above in relation to FIGS. 5 through 7) may be attached to a removable catheter connection hub 66 such as, for example, those disclosed in U.S. Pat. No. 8,038,667 to Racz et al., issued Oct. 18, 2011, the disclosure of which is incorporated herein in its entirety by this reference. Briefly, the removable catheter connection hub 66 may be configured to receive and secure the proximal end 32 of the catheter 12 within the removable catheter connection hub 66. The removable catheter connection hub 66 may be configured to enable other devices or substances to pass through the removable catheter connection hub 66 into the catheter 12 to which the removable catheter connection hub 66 is connected. For example, the removable catheter connection hub 66 may include a connector 68 at a proximal end 70 of the removable catheter connection hub 66. The connector 68 may be configured for connection with infusion tubing, injection ports, syringes, pumps, or other medical fluid transfer apparatus and may comprise, for example, a LUER-LOK® connector. The removable catheter connection hub 66 may include an internal bore (not shown) through which other devices or substances may be conveyed from the proximal end 70 of the removable catheter connection hub 66 to the catheter 12 extending from a distal end 72 of the removable catheter connection hub 66.

In some embodiments, after withdrawal of the support needle 14, the stylet wire 39 of the stylet wire assembly 38 is introduced into the catheter 12 to, for example, prevent kinking of the catheter 12 as it resides in the subject. For example, the catheter assembly 10, 110 may optionally comprise a stylet wire assembly 38' that may be similar to stylet wire assembly 38 discussed above with reference to FIG. 1. As above, the stylet 38' may be configured to reinforce the catheter 12 (e.g., by increasing stiffness of the catheter assembly 10, 110) to reduce the propensity of the catheter 12 to kink while permitting flow of a fluid through the catheter 12. For example, a stylet wire 39' of the stylet wire assembly 38' may comprise a plurality of intertwined or interwoven wires or a plurality of intertwined or interwoven tubes through which a fluid may flow. In some embodiments, the stylet wire 39' promotes flow of a fluid through the catheter 12, for example, by wicking fluid from the proximal end 43 of the stylet wire 39' to the distal end 45 of the stylet wire 39'. The stylet wire 39' may comprise materials, such as, for example, medical grade stainless steel or medical grade titanium. The stylet wire 39' of the stylet wire assembly 38' may lack a stylet hub or cap at the proximal end 43 of the stylet 38'. For example, stylet wire 39' of the stylet wire assembly 38' is coupled to the removable catheter connection hub 46 in some embodiments. In some embodiments, stylet wire 39' is retained within the catheter 12 by the retaining mechanism (e.g., a deformable sleeve) of the removable catheter connection hub 66. In other embodiments, the stylet wire 39' may be embedded within or otherwise attached to the distal end 72 of the removable catheter connection hub 66 and extend from the catheter-receiving portion 74 of the removable catheter connection hub 66. In yet other embodiments, the stylet wire assembly 38 includes a stylet hub or cap as discussed above at the proximal end 43 of the stylet wire 39 (see FIG. 1). For example, the stylet hub may be configured to attach to the connector 70 of the removable catheter connection hub 66 to secure the stylet wire 39 (see FIG. 1) in place and may be configured to permit a fluid to travel through the stylet hub and the catheter 12.

Accordingly, and with combined reference to FIGS. 1, 3, 4, and 8, a catheter assembly 10, 110 or kit for use in administering a sympathetic nerve block may comprise one or more of a catheter 12, a support needle 14, one or more stylets 16, 102, 38, 38', 104, a removable catheter connection hub 66, a FIC (e.g., FIC 100 (FIG. 3)) or other introducer needle, and one or more components for supplying medication through the catheter 12.

Referring to FIG. 9, after the catheter 12 has been inserted through at least one layer of skin and optionally through a cutis 60 (e.g., through one or more of an epidermis layer 58 and a dermis layer 62 of the skin) of the subject and secured to the subject, the catheter 12 may be configured for attachment to a supply of medication (e.g., a pump and associated reservoir) by forming the catheter assembly 10, 110. As depicted, the catheter 12 may be secured within the subject by the one or more tine elements 116 engaging with an internal portion of the subject (e.g., muscle or other tissue). When assembling the catheter assembly 10, 110, the catheter 12 may be secured to the removable catheter connection hub 66. For example, the proximal end 32 of the catheter 12 may be inserted into a catheter-receiving portion 74 at the distal end 72 of the removable catheter connection hub 66. After insertion, the proximal end 32 of the catheter 12 may be secured within the catheter-receiving portion 74 of the removable catheter connection hub 66. For example, the removable catheter connection hub 66 may clamp around the catheter 12 to secure the catheter 12 to the removable catheter connection hub 66, and may optionally form a seal between the catheter 12 and the removable catheter connection hub 66.

The stylet wire 39' (FIG. 8) may be at least partially inserted into the catheter 12. For example, the distal end 45 (see FIG. 8) of the stylet wire 39' extending from (e.g., coupled to or inserted through) the removable catheter connection hub 66 may be inserted into the catheter 12 and extended near, to, or beyond the distal end 34 of the catheter 12. For example, the distal end 45 of the stylet wire 39' may extend between about 1.0 cm from and about 1.0 cm beyond the distal end 34 of the catheter 12 when the stylet wire 39' is disposed within the catheter 12.

In some embodiments, a medication is supplied through the catheter 12 to initiate or maintain a sympathetic nerve block. For example, the practitioner may supply a quantity of the medication by positioning a hypodermic needle or other medication transfer device within the connector 68 of the removable catheter connection hub 66 and forcing flow of the medication through the catheter 12 and out the distal end 34 of the catheter 12 on the lateral side of the vertebra 48 at which the distal end 34 of the catheter 12 is positioned.

Figure 10:
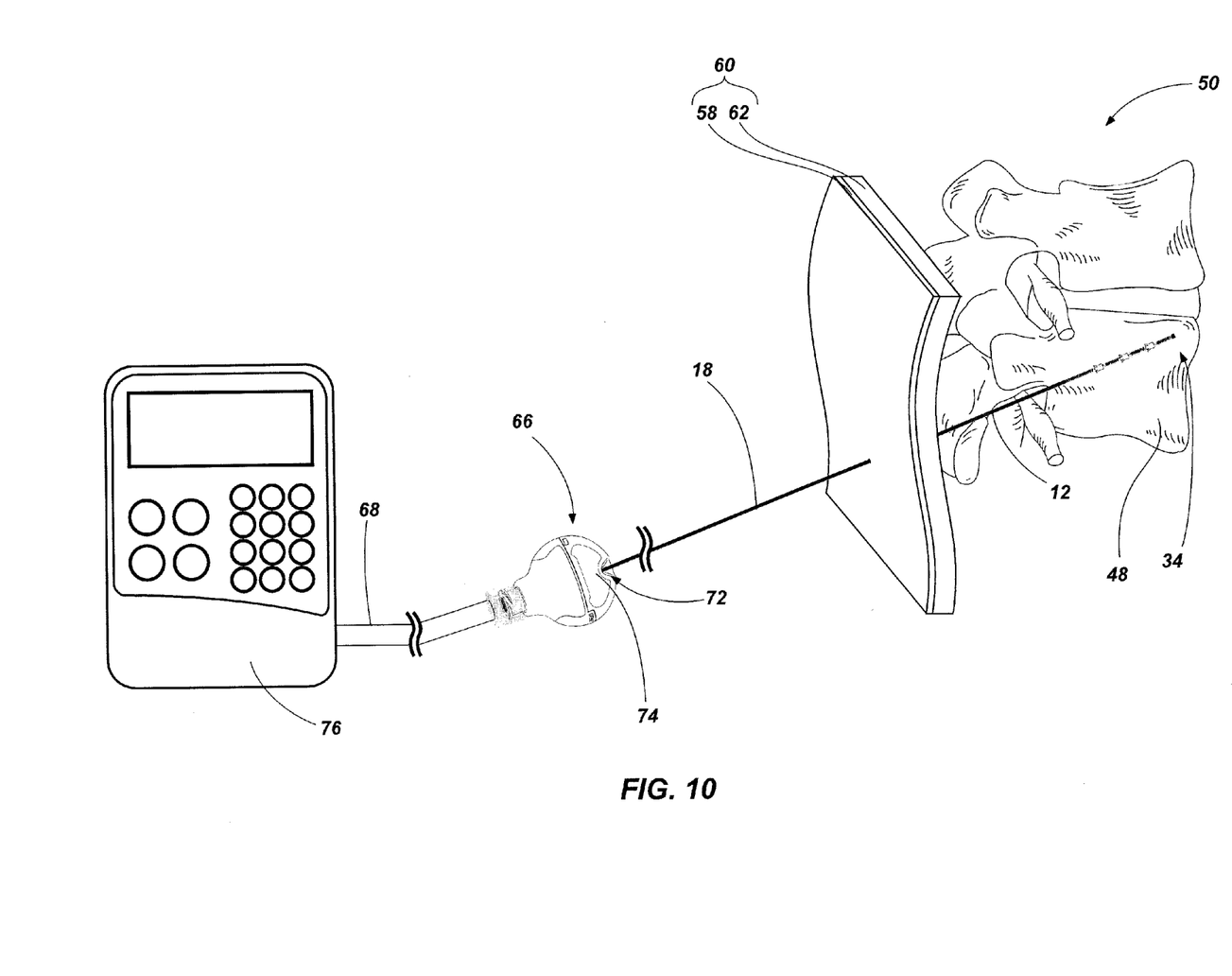
FIG. 10 is a side view of the catheter assembly of FIG. 9 after attachment to a pump.

Referring to FIG. 10, the catheter assembly 10, 110 may be configured for administration of a relatively long-term sympathetic nerve block (e.g., a block lasting one or more days or weeks). For example, the connector 68 of the removable catheter connection hub 66 may be connected to a pump 76 (e.g., an ambulatory infusion pump) configured to supply a medication through the removable catheter connection hub 66 and the catheter 12. The pump 76 may be directly connected to the removable catheter connection hub 66 or may be indirectly connected to the removable catheter connection hub 66, for example, by infusion tubing. The pump 76 may comprise a reservoir (not shown), which may be internal to the pump 76 or external and connected to the pump 76, configured to contain a quantity of medication for maintaining a sympathetic nerve block and a fluid displacement mechanism (e.g., a piston, a diaphragm, a gear, a screw) configured to displace the medication from the reservoir into the subject. Suitable ambulatory infusion pumps are commercially available from Smiths Medical of 600 Cordwainer Drive, 3rd Floor, Norwell, Mass. 02061. The medication in the reservoir may be formulated (with, e.g., an excipient and/or water) to induce a sympathetic nerve block in the subject when administered to a portion of the sympathetic nervous system on a lateral side of the vertebra 48 at which the distal end 34 of the catheter 12 is positioned. For example, the medication may comprise an anesthetic (e.g., bupivacaine or ropivacaine) or an analgesic. The pump 76 may be configured to supply predetermined doses of the medication continuously or intermittently over time to initiate and maintain or simply to maintain a sympathetic nerve block. The medication may be supplied to a portion of the sympathetic nervous system on a lateral side of the vertebra 48 at which the distal end 34 of the catheter 12 is positioned. As the pump 76 displaces medication into the subject, the sympathetic nerve block may be maintained for a longer period of time, using a smaller quantity of medication, or both. For example, the sympathetic nerve block may be maintained for one or more days, one or more weeks, or longer (e.g., one month or more, i.e., 30 to 31 days or more). As a specific, nonlimiting example, the sympathetic nerve block may be maintained for between about 10 days and about 15 days.

The reservoir of the pump 76 requires intermittent refilling within the period during which the sympathetic nerve block is maintained in some embodiments. As a specific, nonlimiting example, the pump 76 may require a daily refill where the pump 76 comprises a 100 mL reservoir and is configured to deliver medication at a rate of about 4 mL/hour. In other embodiments, the initial quantity of medication in the reservoir is sufficient to last the entire duration of treatment.

In some embodiments, the long-term sympathetic nerve block is accompanied by additional procedures. For example, the subject may be exposed to a hyperbaric oxygen environment. In some embodiments, the practitioner administers intradermal or subcutaneous injections of botulinum toxin (e.g., BOTOX®) or transdermal injections of agents formulated to increase vascularity (e.g., nifedipine).

Inducement of a long-term sympathetic nerve block through an indwelling catheter may be useful in treating, for example, foot ulcers, which are a common ailment associated with diabetes. The duration of the sympathetic nerve block may be maintained, for example, until the foot ulcer has closed completely. Other ailments that may be treated using a long-term sympathetic nerve block through an in-dwelling catheter may include, for example, complex regional pain syndrome (CRPS), reflex sympathetic dystrophy (RSD) syndrome, peripheral vascular disease where stem cells may be introduced through a femoral catheter, burn injuries (e.g., burns requiring skin grafts on lower extremities), interstitial cystitis, arterial peripheral ulcers, lymphedema, peripheral skin flaps, long term pain relief of appendicular pain, irritable bowl, or hyperhidrosis.

Once being apprised of the instant disclosure, one of ordinary skill in the art will be able to make and use the devices and assemblies disclosed herein.

What is claimed is:

1. A method of providing a sympathetic nerve block to a subject in need thereof, the method comprising:
  implanting a portion of a catheter into the subject;
  radially stiffening the catheter during insertion of the catheter into the subject with a helical coil spring extending a length of the catheter, the helical coil spring having at least two closed portions and at least one open portion, the at least one open portion having a pitch that is greater than a pitch of the closed portion, the at least one open portion positioned between a first closed portion and a second closed portion of the at least two closed portions;

axially stiffening the catheter and the helical coil spring during insertion of the catheter into the subject with a wire positioned between the catheter and the helical coil spring, the wire coupled at a first end of the wire to the first closed portion of the helical coil spring and coupled at a second end of the wire to the second closed portion of the helical coil spring;

positioning a distal end of the catheter on a lateral side of at least one vertebra of the subject's vertebral column proximate to a portion of a sympathetic nervous system of the subject;

securing a distal portion of the catheter with at least one anchor element extending from an outer surface of the catheter and positioned proximate the distal end of the catheter by engaging the at least one anchor element with at least a portion of the subject when the catheter is inserted within the subject;

delivering a medication to the subject through the open portion of the helical coil spring positioned within the catheter and through at least one opening formed in a sidewall of the catheter positioned at the open portion of the helical spring to create a sympathetic nerve block; and maintaining the sympathetic nerve block for at least one week.

2. The method according to claim 1, further comprising inserting a portion of an introducer cannula into the subject and inserting the portion of the catheter through the introducer cannula.

3. The method according to claim 2, further comprising:
removing a support structure of the introducer cannula; and
removing the introducer cannula.

4. The method according to claim 1, further comprising securing a proximal portion of the catheter to the subject by tunneling the proximal portion of the catheter through the subject to exit the subject at a location remote from an initial insertion point of the catheter.

5. The method according to claim 1, wherein securing the distal portion of the catheter with the at least one anchor element comprises securing the distal portion of the catheter with a plurality of anchor elements coupled to an outer surface of the catheter each including a plurality of tines circumferentially spaced about the anchor element and extending therefrom by engaging at least some of the plurality of tines with at least a portion of the subject when the catheter is inserted within the subject.

6. The method according to claim 1, wherein axially stiffening the catheter and the helical coil spring with the wire comprises selecting the wire to be attached at the first end of the wire to the first closed portion of the helical coil spring with a weld bead at a distalmost end of the catheter.

7. The method according to claim 1, further comprising inserting a stylet wire into the catheter before inserting the portion of the catheter into the subject or after inserting the portion of the catheter into the subject.

8. The method according to claim 7, wherein inserting the stylet wire into the catheter comprises positioning the stylet wire within the catheter such that a distal end of the stylet wire extends at least to the distal end of the catheter.

9. The method according to claim 1, further comprising coupling a removable catheter connection hub to a pump for supplying predetermined doses of the medication.

10. The method according to claim 1, further comprising maintaining the sympathetic nerve block for more than one week and less than one month.

11. A method of alleviating pain in a lower extremity of a subject, the method comprising:
implanting a portion of a catheter into a subject;
positioning a distal end of the catheter at a location on a lateral side of at least one lumbar vertebra of the subject proximate to a portion of a sympathetic nervous system of the subject;
maintaining the catheter in the subject for a continuous period of more than one day and less than two months;
reinforcing the distal end of the catheter to assist in maintaining the catheter at the location within the subject during the continuous period, the reinforcing the distal end of the catheter comprising:
radially reinforcing the catheter with a helical coil spring, the helical coil spring having at least one closed portion and at least one open portion, the at least one open portion having a pitch that is greater than a pitch of the closed portion; and
axially reinforcing one or more of the catheter and the helical coil spring with a wire positioned between the catheter and the helical coil spring, the wire coupled at a first end of the wire to a distal portion of the helical coil spring and coupled at a second end of the wire to a proximal portion of the helical coil spring;
securing the catheter within the subject with an anchoring element positioned within the subject to substantially prevent movement of the subject from substantially dislodging the distal end of the catheter from the location during the continuous period; and
delivering an anesthetic to the subject through the catheter from an ambulatory pump while enabling the subject to be mobile during the continuous period.

12. The method according to claim 11, wherein the subject is human and further comprising positioning the distal end of the catheter adjacent to the L4 vertebra.

13. The method according to claim 11, wherein securing the catheter within the subject further comprises securing a distal portion of the catheter with a plurality of anchor elements coupled to an outer surface of the catheter each including a plurality of tines circumferentially spaced about the anchor element and extending therefrom by engaging at least some of the plurality of tines with at least a portion of the subject when the catheter is inserted within the subject.

14. A method of providing a sympathetic nerve block to a subject in need thereof, the method comprising:
implanting a portion of a catheter into the subject through an introducer needle, the catheter having a proximal end and a distal end and comprising at least one tine element coupled to an outer surface of the catheter and positioned proximate the distal end of the catheter;
positioning the distal end of the catheter on a lateral side of at least one vertebra of the subject's vertebral column proximate to a portion of a sympathetic nervous system of the subject;
securing a distal portion of the catheter by engaging the at least one anchor element with at least a portion of the subject when the catheter is inserted within the subject;
radially reinforcing the catheter to assist in maintaining the catheter at a location within the subject with a helical coil spring positioned proximate the distal end of the catheter; and
axially reinforcing the catheter to assist in maintaining the catheter at the location within the subject with a wire positioned within the catheter proximate the distal end of the catheter, a first portion of the wire coupled to a distal portion of the helical coil spring and a second portion of the wire coupled to a proximal portion of the helical coil spring;

delivering a medication to the subject through the catheter from an ambulatory dispensing device to create a sympathetic nerve block for more than one day and less than two months while enabling the subject to be mobile; and after delivering the medication to the subject through the catheter to create the sympathetic nerve block for more than one day and less than two months, removing the catheter from the subject.

15. The method according to claim 14, further comprising securing the proximal end of the catheter in a catheter connection hub.

16. The method according to claim 15, further comprising inserting a stylet wire into the catheter and securing the stylet wire with the catheter connection hub.

17. The method according to claim 16, further comprising extending the stylet wire at least to the distal end the catheter.

18. The method according to claim 14, further comprising passing a fluid through an open portion of the helical coil spring to an opening formed in a sidewall of the catheter, the open portion of the helical coil spring positioned proximate the distal end of the catheter and the at least one time element.

19. The method according to claim 14, further comprising securing the distal portion of the catheter with at least three tine elements, each having a plurality of tines circumferentially spaced about the tine element.

20. A method of alleviating pain in a lower extremity of a subject, the method comprising:

implanting a portion of a catheter having a proximal end and a distal end and at least one anchor element coupled to an outer surface of the catheter into the subject through an introducer needle;

securing a distal portion of the catheter by engaging the at least one anchor element with at least the psoas major muscle of the subject when the catheter is inserted within the subject;

securing the proximal end of the catheter in a catheter connection hub;

maintaining the catheter in the subject for between one day and two months;

radially reinforcing the catheter to assist in maintaining the catheter within the subject with a helical coil spring positioned proximate the distal end of the catheter; and axially reinforcing the catheter to assist in maintaining the catheter within the subject with a wire positioned within the catheter proximate the distal end of the catheter, a first portion of the wire coupled to a first portion of the helical coil spring and a second portion of coupled to a proximal portion of the helical coil spring; and delivering a medication to the subject through the catheter.

* * * * *